United States Patent
Jarral et al.

(10) Patent No.: US 11,141,275 B2
(45) Date of Patent: Oct. 12, 2021

(54) PERCUTANEOUS REPAIR OF MITRAL PROLAPSE

(71) Applicant: BOSTON SCIENTIFIC SCIMED, INC., Maple Grove, MN (US)

(72) Inventors: Omar Jarral, London (GB); Patricia McAfee, Galway (IE); Aiden Flanagan, Galway (IE); Tim O'Connor, Galway (IE); Jan Weber, Maastricht (NL)

(73) Assignee: Boston Scientific Scimed, Inc., Maple Grove, MN (US)

( * ) Notice: Subject to any disclaimer, the term of this patent is extended or adjusted under 35 U.S.C. 154(b) by 318 days.

(21) Appl. No.: 16/135,560

(22) Filed: Sep. 19, 2018

(65) Prior Publication Data
US 2019/0083264 A1  Mar. 21, 2019

Related U.S. Application Data

(60) Provisional application No. 62/560,508, filed on Sep. 19, 2017.

(51) Int. Cl.
*A61F 2/24* (2006.01)
*A61B 17/064* (2006.01)
(Continued)

(52) U.S. Cl.
CPC ........ *A61F 2/2466* (2013.01); *A61B 17/0401* (2013.01); *A61B 17/064* (2013.01);
(Continued)

(58) Field of Classification Search
CPC . A61B 17/0401; A61B 17/064; A61B 17/068; A61B 2017/0647;
(Continued)

(56) References Cited

U.S. PATENT DOCUMENTS

| | | | |
|---|---|---|---|
| 5,634,936 A | 6/1997 | Linden et al. | |
| 5,853,422 A | 12/1998 | Huebsch et al. | |

(Continued)

FOREIGN PATENT DOCUMENTS

| | | |
|---|---|---|
| DE | 102008045877 A1 | 3/2010 |
| WO | 2006039199 A2 | 4/2006 |

(Continued)

OTHER PUBLICATIONS

"International Search Report and Written Opinion" dated Nov. 29, 2017.
(Continued)

*Primary Examiner* — Tuan V Nguyen
(74) *Attorney, Agent, or Firm* — Seager, Tufte & Wickhem LLP

(57) ABSTRACT

A mitral valve leaflet repair system may include a delivery catheter having at least one lumen extending proximally from a distal end of the delivery catheter, a plurality of anchor elements disposed within the at least one lumen, each of the plurality of anchor elements being configured to extend through one layer of mitral valve leaflet tissue, and a securing element configured to secure at least two of the plurality of anchor elements together on one side of the mitral valve leaflet tissue. The at least one lumen may include a suction lumen configured to grasp a mitral valve leaflet prior to extending the plurality of anchor elements through one layer of mitral valve leaflet tissue.

20 Claims, 17 Drawing Sheets

(51) Int. Cl.
*A61B 17/04* (2006.01)
*A61B 17/068* (2006.01)
*A61B 17/00* (2006.01)
*A61B 17/30* (2006.01)

(52) U.S. Cl.
CPC .......... *A61B 17/068* (2013.01); *A61F 2/2445* (2013.01); *A61F 2/2463* (2013.01); *A61B 17/0466* (2013.01); *A61B 2017/00243* (2013.01); *A61B 2017/00477* (2013.01); *A61B 2017/00783* (2013.01); *A61B 2017/00876* (2013.01); *A61B 2017/0408* (2013.01); *A61B 2017/0412* (2013.01); *A61B 2017/0448* (2013.01); *A61B 2017/0464* (2013.01); *A61B 2017/0645* (2013.01); *A61B 2017/0647* (2013.01); *A61B 2017/306* (2013.01); *A61F 2210/009* (2013.01); *A61F 2210/0014* (2013.01); *A61F 2220/0008* (2013.01); *A61F 2220/0016* (2013.01); *A61F 2250/0067* (2013.01); *A61F 2250/0098* (2013.01)

(58) Field of Classification Search
CPC ........... A61B 2017/0648; A61F 2/2466; A61F 2/2445; A61F 2/2463; A61F 2/2457
See application file for complete search history.

(56) References Cited

U.S. PATENT DOCUMENTS

| | | | |
|---|---|---|---|
| 6,024,756 A | 2/2000 | Huebsch et al. | |
| 6,117,159 A | 9/2000 | Huebsch et al. | |
| 6,269,819 B1 | 8/2001 | Oz et al. | |
| 6,270,515 B1 | 8/2001 | Linden et al. | |
| 6,312,446 B1 | 11/2001 | Huebsch et al. | |
| 6,575,971 B2 | 6/2003 | Hauck et al. | |
| 6,629,534 B1 | 10/2003 | St. Goar et al. | |
| 6,752,813 B2 | 6/2004 | Goldfarb et al. | |
| 6,926,715 B1 | 8/2005 | Hauck et al. | |
| 6,997,950 B2 | 2/2006 | Chawla | |
| 7,335,213 B1 | 2/2008 | Hyde et al. | |
| 7,404,824 B1 | 7/2008 | Webler et al. | |
| 7,464,712 B2 | 12/2008 | Oz et al. | |
| 7,509,959 B2 | 3/2009 | Oz et al. | |
| 7,563,273 B2 | 7/2009 | Goldfarb et al. | |
| 7,608,091 B2 | 10/2009 | Goldfarb et al. | |
| 7,632,308 B2 | 12/2009 | Loulmet | |
| 7,635,329 B2 | 12/2009 | Goldfarb et al. | |
| 7,635,386 B1 | 12/2009 | Gammie | |
| 7,704,269 B2 | 4/2010 | St. Goar et al. | |
| 7,753,923 B2 | 7/2010 | St. Goar et al. | |
| 7,758,586 B2 | 7/2010 | Muto et al. | |
| 7,927,370 B2 | 4/2011 | Webler et al. | |
| 7,938,827 B2 | 5/2011 | Hauck et al. | |
| 7,998,151 B2 | 8/2011 | St. Goar et al. | |
| 8,029,518 B2 | 10/2011 | Goldfarb et al. | |
| 8,052,592 B2 | 11/2011 | Goldfarb et al. | |
| 8,070,804 B2 | 12/2011 | Hyde et al. | |
| 8,133,239 B2 | 3/2012 | Oz et al. | |
| 8,187,299 B2 | 5/2012 | Goldfarb et al. | |
| 8,216,230 B2 | 7/2012 | Hauck et al. | |
| 8,323,334 B2 | 12/2012 | Deem et al. | |
| 8,357,193 B2 | 1/2013 | Phan et al. | |
| 8,454,632 B2 | 6/2013 | Binmoeller et al. | |
| 8,721,665 B2 | 5/2014 | Oz et al. | |
| 8,734,505 B2 | 5/2014 | Goldfarb et al. | |
| 8,740,918 B2 | 6/2014 | Seguin | |
| 8,961,594 B2 | 2/2015 | Maisano et al. | |
| 8,961,596 B2 | 2/2015 | Maisano et al. | |
| 9,044,246 B2 | 6/2015 | Goldfarb et al. | |
| 9,241,702 B2 | 1/2016 | Maisano et al. | |
| 9,427,237 B2 | 8/2016 | Oz et al. | |
| 9,532,874 B2 | 1/2017 | Griffin et al. | |
| 2001/0005787 A1 | 6/2001 | Oz et al. | |
| 2002/0013571 A1 | 1/2002 | Goldfarb et al. | |
| 2003/0093071 A1 | 5/2003 | Hauck et al. | |
| 2003/0120341 A1 | 6/2003 | Shennib et al. | |
| 2004/0002719 A1 | 1/2004 | Oz et al. | |
| 2004/0003819 A1 | 1/2004 | St. Goar et al. | |
| 2004/0030382 A1 | 2/2004 | St. Goar et al. | |
| 2004/0039442 A1 | 2/2004 | St. Goar et al. | |
| 2004/0199183 A1 | 10/2004 | Oz et al. | |
| 2004/0225300 A1 | 11/2004 | Goldfarb et al. | |
| 2005/0004583 A1 | 1/2005 | Oz et al. | |
| 2005/0021056 A1 | 1/2005 | St. Goar et al. | |
| 2005/0021057 A1 | 1/2005 | St. Goar et al. | |
| 2005/0033446 A1 | 2/2005 | Deem et al. | |
| 2005/0119734 A1 | 6/2005 | Spence et al. | |
| 2005/0149014 A1 | 7/2005 | Hauck et al. | |
| 2005/0240202 A1 | 10/2005 | Shennib et al. | |
| 2006/0030885 A1 | 2/2006 | Hyde | |
| 2007/0050019 A1* | 3/2007 | Hyde .................... A61F 2/2445 623/2.11 |
| 2007/0073337 A1 | 3/2007 | Abbott et al. | |
| 2007/0112425 A1 | 5/2007 | Schaller et al. | |
| 2007/0118213 A1 | 5/2007 | Loulmet | |
| 2008/0051807 A1 | 2/2008 | St. Goar et al. | |
| 2008/0125860 A1 | 5/2008 | Webler et al. | |
| 2008/0125861 A1 | 5/2008 | Webler et al. | |
| 2008/0167714 A1 | 7/2008 | St. Goar et al. | |
| 2008/0183194 A1 | 7/2008 | Goldfarb et al. | |
| 2008/0228165 A1* | 9/2008 | Spence ................. A61F 2/2466 604/510 |
| 2009/0198322 A1 | 8/2009 | Deem et al. | |
| 2009/0270858 A1 | 10/2009 | Hauck et al. | |
| 2009/0276037 A1 | 11/2009 | Oz et al. | |
| 2010/0016958 A1 | 1/2010 | St. Goar et al. | |
| 2010/0049311 A1 | 2/2010 | Loulmet | |
| 2010/0217283 A1 | 8/2010 | St. Goar et al. | |
| 2011/0011917 A1 | 1/2011 | Loulmet | |
| 2011/0015730 A1* | 1/2011 | Machold ............ A61B 17/0401 623/2.11 |
| 2011/0264208 A1 | 10/2011 | Duffy et al. | |
| 2011/0307055 A1 | 12/2011 | Goldfarb et al. | |
| 2012/0179184 A1 | 7/2012 | Orlov | |
| 2012/0296349 A1 | 11/2012 | Smith et al. | |
| 2013/0013056 A1 | 1/2013 | Chawla | |
| 2014/0114403 A1 | 4/2014 | Dale et al. | |
| 2014/0128970 A1 | 5/2014 | Griffin et al. | |
| 2014/0243860 A1 | 8/2014 | Morris et al. | |
| 2014/0257341 A1 | 9/2014 | Eidenschink et al. | |
| 2014/0276971 A1 | 9/2014 | Kovach | |
| 2014/0296878 A1 | 10/2014 | Oz et al. | |
| 2015/0045879 A1 | 2/2015 | Longoria et al. | |
| 2015/0057682 A1 | 2/2015 | Kovach | |
| 2015/0223793 A1 | 8/2015 | Goldfarb et al. | |
| 2015/0230919 A1 | 8/2015 | Chau et al. | |
| 2015/0257883 A1 | 9/2015 | Basude et al. | |
| 2015/0313620 A1* | 11/2015 | Suri ..................... A61B 17/29 606/205 |
| 2016/0354082 A1 | 12/2016 | Oz et al. | |
| 2017/0007405 A1 | 1/2017 | Griffin et al. | |
| 2019/0076248 A1* | 3/2019 | McAfee ................ A61F 2/2445 |

FOREIGN PATENT DOCUMENTS

| | | |
|---|---|---|
| WO | 2007009021 A2 | 1/2007 |
| WO | 2007070753 A2 | 6/2007 |
| WO | 2011033508 A1 | 3/2011 |
| WO | 2016064748 A1 | 4/2016 |

OTHER PUBLICATIONS

Glower, "Surgical Approaches to Mitral Regurgitation," Journal of the American College of Cardiology, vol. (60): 8 pages, 2012.
International Search Report and Written Opinion dated Dec. 20, 2018 for International Application No. PCT/US2018/051752.

* cited by examiner

PERCUTANEOUS REPAIR OF MITRAL PROLAPSE

CROSS-REFERENCE TO RELATED APPLICATIONS

This application claims the benefit of priority under 35 U.S.C. § 119 to U.S. Provisional Application Ser. No. 62/560,508, filed Sep. 19, 2017, the entirety of which is incorporated herein by reference.

TECHNICAL FIELD

The present disclosure pertains to medical devices and methods for using medical devices. More particularly, the present disclosure pertains to aspects of medical devices and/or means to deliver and release medical devices for percutaneously treating degenerative mitral regurgitation by isolating redundant tissue in mitral valve leaflets.

BACKGROUND

A wide variety of intracorporeal medical devices have been developed for medical use, for example, surgical and/or intravascular use. Some of these devices include guidewires, catheters, medical device delivery systems (e.g., for stents, grafts, replacement valves, occlusive medical devices, etc.), and the like. These devices are manufactured by any one of a variety of different manufacturing methods and may be used according to any one of a variety of methods. There is an ongoing need to provide alternative medical devices as well as alternative methods for manufacturing and/or using medical devices.

SUMMARY

In a first aspect, a mitral valve leaflet repair system may comprise a delivery catheter having at least one lumen extending proximally from a distal end of the delivery catheter; a plurality of anchor elements disposed within the at least one lumen, each of the plurality of anchor elements being configured to extend through one layer of mitral valve leaflet tissue; and a securing element configured to secure at least two of the plurality of anchor elements together on one side of the mitral valve leaflet tissue. The at least one lumen may comprise a suction lumen configured to grasp a mitral valve leaflet prior to extending the plurality of anchor elements through one layer of mitral valve leaflet tissue.

In addition or alternatively, and in a second aspect, the at least one lumen further comprises a plurality of anchor lumens, wherein at least one of the plurality of anchor elements is disposed within each of two or more of the plurality of anchor lumens.

In addition or alternatively, and in a third aspect, at least one of the plurality of anchor elements is disposed within the suction lumen.

In addition or alternatively, and in a fourth aspect, at least one of the plurality of anchor elements comprises a rivet.

In addition or alternatively, and in a fifth aspect, at least one of the plurality of anchor elements comprises a self-expanding frame.

In addition or alternatively, and in a sixth aspect, at least one of the plurality of anchor elements comprises a screw-type fastener, wherein rotation of a rotatable insert expands a distal portion of its respective anchor element.

In addition or alternatively, and in a seventh aspect, securing two of the plurality of anchor elements together forms a fold in the one layer of mitral valve leaflet tissue, the fold being disposed between the at least two of the plurality of anchor elements.

In addition or alternatively, and in an eighth aspect, the securing element is configured to be disposed around at least a portion of a perimeter of each of the at least two of the plurality of anchor elements.

In addition or alternatively, and in a ninth aspect, the securing element comprises a shape memory material.

In addition or alternatively, and in a tenth aspect, the securing element forms a closed loop around the at least two of the plurality of anchor elements.

In addition or alternatively, and in an eleventh aspect, the securing element comprises a magnetic attraction between each of the at least two of the plurality of anchor elements.

In addition or alternatively, and in a twelfth aspect, a method of treating mitral valve prolapse may comprise: percutaneously inserting a delivery catheter to a left atrium of a heart; securing a distal end of the delivery catheter to a mitral valve leaflet using a suction lumen extending through the delivery catheter; inserting a plurality of anchor elements into the mitral valve leaflet from the distal end of the delivery catheter at spaced-apart locations; translating two of the plurality of anchor elements closer together; and securing the at least two of the plurality of anchor elements together on one side of the mitral valve leaflet.

In addition or alternatively, and in a thirteenth aspect, translating two of the plurality of anchor elements closer together further comprises forming a fold in the mitral valve leaflet, the fold being disposed between the at least two of the plurality of anchor elements.

In addition or alternatively, and in a fourteenth aspect, the mitral valve leaflet is released from the distal end of the delivery catheter after inserting each anchor element, and the distal end of the delivery catheter is re-secured to the mitral valve leaflet before inserting each subsequent anchor element into the mitral valve leaflet.

In addition or alternatively, and in a fifteenth aspect, the plurality of anchor elements is inserted along lateral boundaries of prolapsed tissue of the mitral valve leaflet, such that the at least two of the plurality of anchor elements are disposed on opposing sides of the prolapsed tissue.

In addition or alternatively, and in a sixteenth aspect, inserting the plurality of anchor elements into the mitral valve leaflet includes inserting each anchor element through only a single thickness of the mitral valve leaflet.

In addition or alternatively, and in a seventeenth aspect, a method of treating mitral valve prolapse may comprise: percutaneously inserting a delivery catheter to a left atrium of a heart; securing a distal end of the delivery catheter to a mitral valve leaflet using a suction lumen extending through the delivery catheter; inserting two or more pairs of anchor elements into the mitral valve leaflet from the distal end of the delivery catheter at a first relative location, wherein the anchor elements of each pair of anchor elements are spaced apart from each other at the first relative location; translating each pair of anchor elements to a second relative location, wherein the anchor elements of each pair of anchor elements are closer together than at the first relative location; and securing each pair of anchor elements together at the second relative location on one side of the mitral valve leaflet.

In addition or alternatively, and in an eighteenth aspect, translating each pair of anchor elements to the second relative location further comprises forming a fold in the mitral valve leaflet, the fold being disposed between each pair of anchor elements.

In addition or alternatively, and in a nineteenth aspect, the mitral valve leaflet is released from the distal end of the delivery catheter after inserting each pair of anchor elements, and the distal end of the delivery catheter is resecured to the mitral valve leaflet before inserting each subsequent pair of anchor elements into the mitral valve leaflet.

In addition or alternatively, and in a twentieth aspect, the two or more pairs of anchor elements are disposed within lumens of the delivery catheter other than the suction lumen prior to insertion into the mitral valve leaflet.

The above summary of some embodiments, aspects, and/or examples is not intended to describe each embodiment or every implementation of the present disclosure. The figures and the detailed description which follows more particularly exemplify these embodiments.

BRIEF DESCRIPTION OF THE DRAWINGS

The disclosure may be more completely understood in consideration of the following detailed description of various embodiments in connection with the accompanying drawings, in which.

Figure 1:
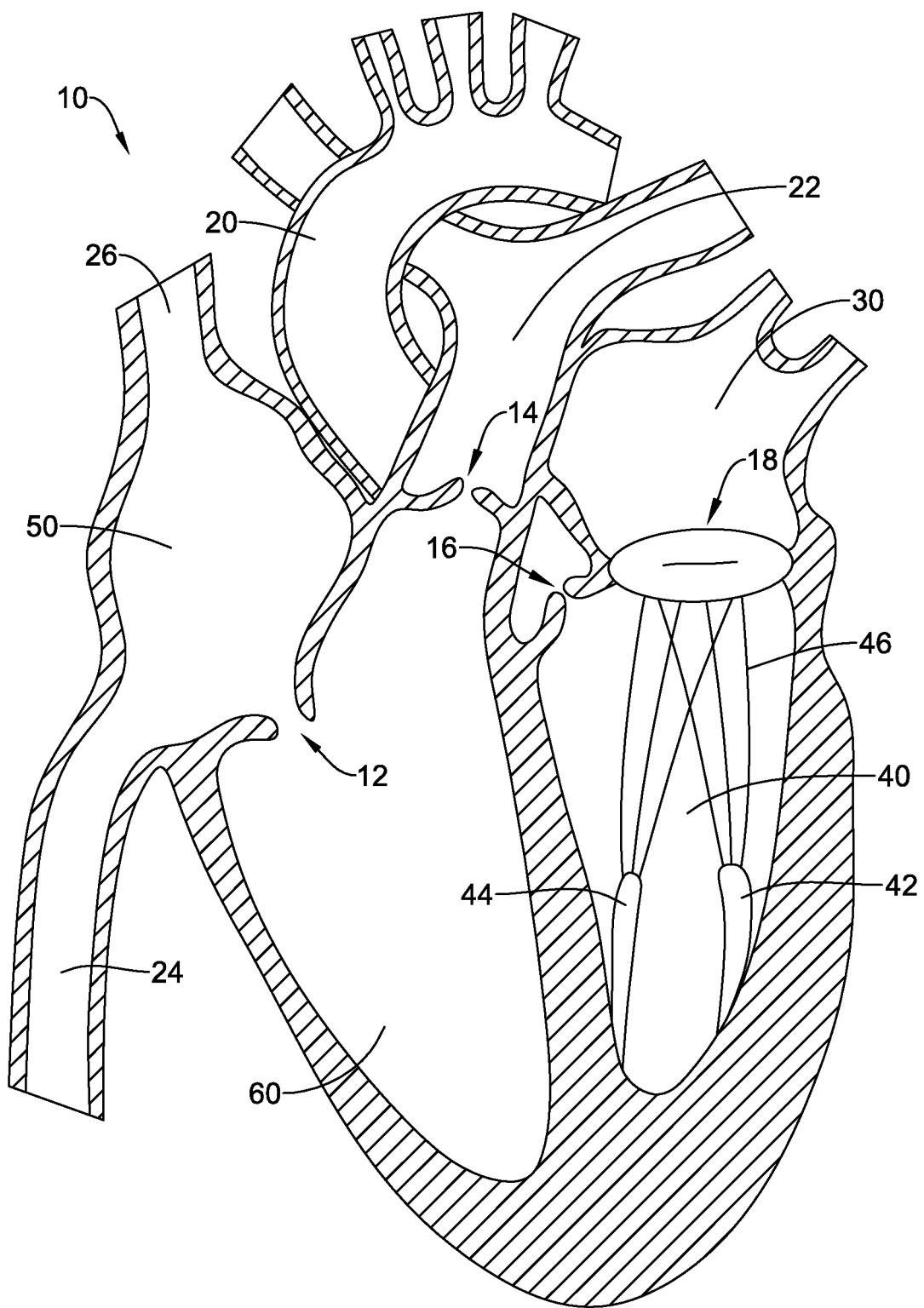
FIG. 1 is a partial cut-away view of an example heart.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention. However, in the interest of clarity and ease of understanding, while every feature and/or element may not be shown in each drawing, the feature(s) and/or element(s) may be understood to be present regardless, unless otherwise specified.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosed invention are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device. Still other relative terms, such as "axial", "circumferential", "longitudinal", "lateral", "radial", etc. and/or variants thereof generally refer to direction and/or orientation relative to a central longitudinal axis of the disclosed structure or device.

The terms "extent" and/or "maximum extent" may be understood to mean a greatest measurement of a stated or identified dimension, while the term "minimum extent" may be understood to mean a smallest measurement of a stated or identified dimension. For example, "outer extent" may be understood to mean a maximum outer dimension, "radial extent" may be understood to mean a maximum radial dimension, "longitudinal extent" may be understood to mean a maximum longitudinal dimension, etc. Each instance of an "extent" may be different (e.g., axial, longitudinal, lateral, radial, circumferential, etc.) and will be apparent to the skilled person from the context of the individual usage. Generally, an "extent" or "maximum extent" may be considered a greatest possible dimension measured according to the intended usage. Alternatively, a "minimum extent" may be considered a smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other or to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

Diseases and/or medical conditions that impact the cardiovascular system are prevalent throughout the world. Some mammalian hearts (e.g., human, etc.) include four heart valves: a tricuspid valve 12, a pulmonary valve 14, an aortic valve 16, and a mitral valve 18, as seen in an example heart 10 illustrated in FIG. 1. The purpose of the heart valves is to control blood flow into the heart 10 from the inferior vena cava 24 and/or the superior vena cava 26, through the heart 10, and out of the heart 10 into the major blood vessels connected to the heart 10, such as the aorta 20, the pulmonary artery 22, for example. Each heart valve may have a plurality of valve leaflets configured to shift between an open configuration permitting fluid flow through the heart valve in an antegrade direction, and a closed configuration wherein free edges of the valve leaflets coapt to substantially prevent fluid flow through the heart valve in a retrograde direction. The heart 10 may also include a left atrium 30, a left ventricle 40, a right atrium 50, and a right ventricle 60. The left ventricle 40 may include a first papillary muscle 42 attached to and/or extending from a wall of the left ventricle 40, a second papillary muscle 44 attached to and/or extending from the wall of the left ventricle 40, and a plurality of chordae 46 connecting the first papillary muscle 42 and the second papillary muscle 44 to the leaflets of the mitral valve 18. In a normally functioning heart valve, blood is permitted to pass or flow downstream through the heart valve (e.g., from an atrium to a ventricle, from a ventricle to an artery, etc.) when the heart valve is open (e.g., during diastole), and when the heart valve is closed (e.g., during systole), blood is prevented from passing or flowing back upstream through the heart valve (e.g., from a ventricle to an atrium, etc.).

In some instances, when regurgitation (e.g., mitral regurgitation) occurs, a heart valve (e.g., the mitral valve 18) fails to open and/or close properly such that blood is permitted to pass or flow back upstream through the heart valve (e.g., from a ventricle to an atrium, etc.). In some cases, the defective heart valve may have leaflets that may not close, or may not be capable of closing, completely. In some instances, secondary or functional mitral regurgitation may be a secondary effect of left ventricular dysfunction, where left ventricular dilatation and/or distension caused by ischemic or idiopathic cardiomyopathy, for example, results in annular dilatation and/or distension of the left ventricle 40 and papillary muscle displacement with subsequent leaflet tethering and insufficient coaptation of the mitral leaflets during systole. In some instances, degenerative mitral regurgitation may involve redundant excessive tissue in part of the heart valve and/or the heart valve leaflets (e.g., mitral valve prolapse). Surgical methods of treating degenerative mitral regurgitation may include resection of the prolapsed segment and placement of an annuloplasty ring to stabilize the valve (in many cases but not necessarily every case). However, such methods may be invasive and/or unsuitable for frail patients who are not qualified surgical candidates.

Disclosed herein are apparatus, medical devices, and/or methods that may be used to diagnose, treat, and/or repair a portion of the cardiovascular system. One possible remedy is percutaneous procedure which may isolate redundant leaflet tissue without removing any of the tissue, thereby permitting the heart valve leaflets to properly close the heart valve to the passage of blood. The disclosed mitral valve leaflet repair system, method(s), and associated medical device(s) may be performed/used percutaneously via minimally-invasive intravascular techniques, or in an alternative method, using open-heart surgical methods. The device(s) and method(s) disclosed herein may also provide a number of additional desirable features and/or benefits as described in more detail below. For the purpose of this disclosure, the discussion below is directed toward repairing the mitral valve 18 and will be so described in the interest of brevity. This, however, is not intended to be limiting as the skilled person will recognize that the following discussion may also apply to the aortic valve or another heart valve with no or minimal changes to the structure and/or scope of the disclosure.

Figure 2:
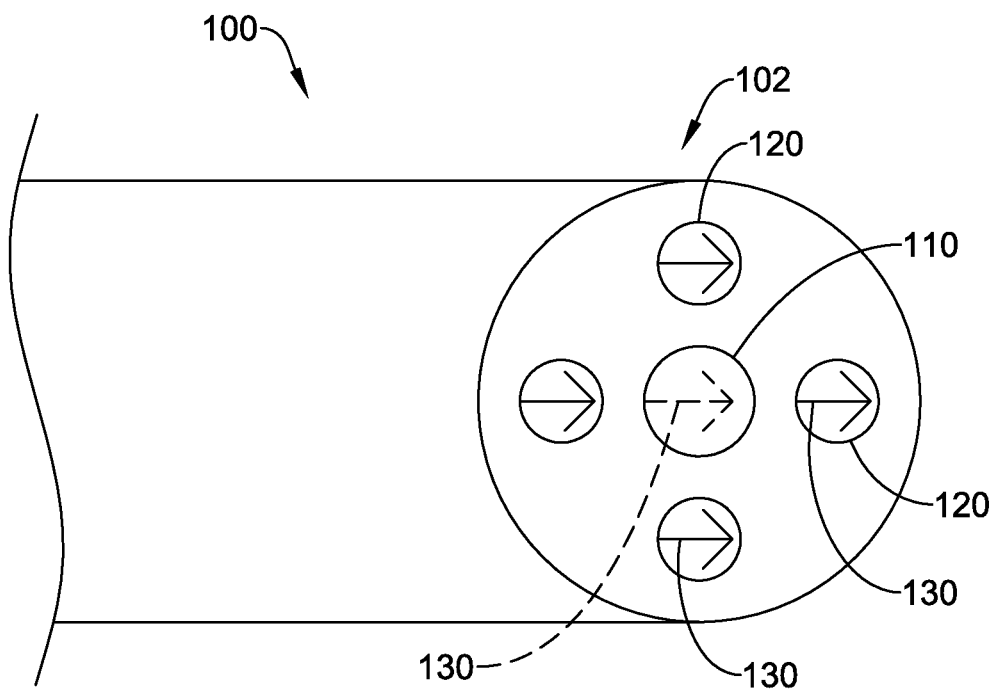
FIG. 2 illustrates an example delivery catheter.

FIG. 2 illustrates an example delivery catheter 100 of a mitral valve leaflet repair system. The mitral valve leaflet repair system may include a plurality of anchor elements 130, shown schematically in FIG. 2 as an arrowhead, wherein each of the plurality of anchor elements 130 is configured to extend through one layer of mitral valve leaflet tissue, as will be described below. The mitral valve leaflet repair system may further comprise a securing element 140 (e.g., FIGS. 13-15), also described in more detail below, configured to secure at least two of the plurality of anchor elements 130 together on one side (e.g., on an atrial side, on a ventricular side) of the mitral valve leaflet tissue.

The delivery catheter 100 may include at least one lumen extending proximally from a distal end 102 of the delivery catheter 100. The plurality of anchor elements 130 may be disposed within the at least one lumen, as shown in FIG. 2 for example. In some embodiments, the at least one lumen may comprise a suction lumen 110 configured to grasp and/or hold, and/or to secure the distal end 102 of the delivery catheter 100 to, a surface (e.g., a "top" or atrial surface) of a mitral valve leaflet during a mitral valve leaflet repair procedure. The suction lumen 110 may be in fluid communication with a source of suction. In some embodiments, an alternative gripping mechanism, for example a claw-like mechanism, may be used to hold the mitral valve leaflet during a mitral valve leaflet repair procedure. In some embodiments, at least one of the plurality of anchor elements 130 may be disposed within the suction lumen 110, as seen in phantom in FIG. 2.

In some embodiments, the at least one lumen may further comprise a plurality of anchor lumens 120. At least one of the plurality of anchor elements 130 may be disposed within each of the plurality of anchor lumens 120, as seen in FIG. 2. In some embodiments, the suction lumen 110 may also be and/or function as one of the plurality of anchor lumens 120. In some embodiments, the delivery catheter 100 may comprise a single lumen extending from a proximal end to the distal end 102, wherein the single lumen functions as both a suction lumen and an anchor lumen. In some embodiments, the plurality of anchor elements 130 may be disposed within the single lumen. In some embodiments, at least one of the plurality of anchor elements 130 may be disposed within each of two or more of the plurality of anchor lumens 120.

In at least some embodiments, each of the at least one lumen may have and/or include a pushing member and/or mechanism (not shown) configured to advance the plurality of anchor elements 130 distally out of the delivery catheter 100 and into and/or through one layer and/or a single thickness of mitral valve leaflet tissue. In some embodiments, each of the plurality of anchor lumens 120 may have and/or include a pushing member and/or mechanism configured to advance the plurality of anchor elements 130 distally out of the delivery catheter 100 and into and/or through one layer and/or a single thickness of mitral valve leaflet tissue. In some embodiments, the suction lumen 110 may have and/or include a pushing member and/or mechanism configured to advance the plurality of anchor elements 130 distally out of the delivery catheter 100 and into and/or through one layer and/or a single thickness of mitral valve leaflet tissue. In some embodiments, each pushing member and/or mechanism may be configured to advance one of the plurality of anchor elements 130 distally out of the delivery catheter 100 and into and/or through one layer and/or a single thickness of mitral valve leaflet tissue. In some embodiments, each pushing member and/or mechanism may be configured to advance only one of the plurality of anchor elements 130 distally out of the delivery catheter 100 and into and/or through one layer and/or a single thickness of mitral valve leaflet tissue. In some embodiments, each pushing member and/or mechanism may be configured to advance more than one of the plurality of anchor elements 130 distally out of the delivery catheter 100 and into and/or through one layer and/or a single thickness of mitral valve leaflet tissue.

In some embodiments, each pushing member and/or mechanism may extend through its respective lumen. In some embodiments, each pushing member and/or mechanism may extend out proximally past the proximal end of the delivery catheter 100.

In some embodiments, each pushing member and/or mechanism may be disposed entirely within the delivery catheter 100. In some embodiments, each pushing member and/or mechanism may be disposed entirely within the delivery catheter 100, except for an activation and/or actuation means proximate the proximal end of the delivery catheter 100. Various combinations of these features are also contemplated. Some suitable but non-limiting materials for the delivery catheter 100, the pushing member and/or mechanism, and/or other associated components, for example metallic materials, polymer materials, composite materials, etc., are described below.

Figure 3:
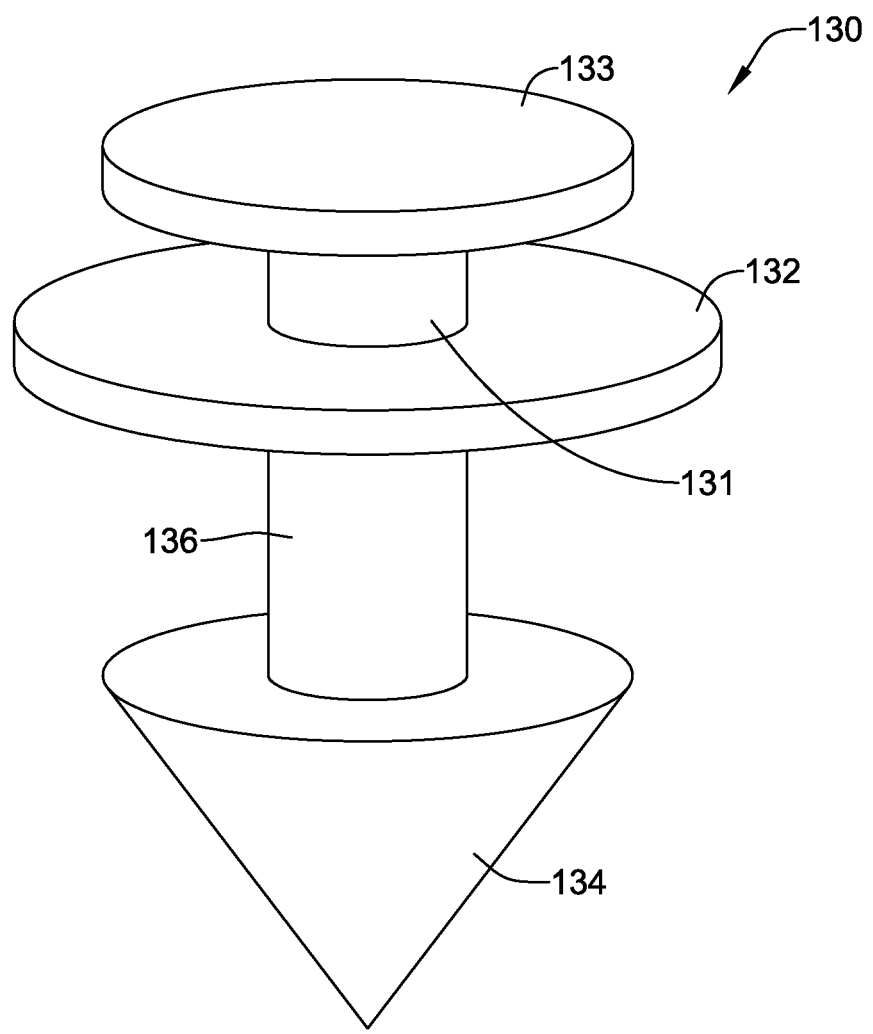
FIG. 3 illustrates an example anchor element.

FIG. 3 illustrates an example anchor element 130 comprising a rivet. In at least some embodiments, the anchor element 130 may be a rivet having a fixed configuration. In some embodiments, the anchor element 130 may include a flattened head portion 132, a pointed and/or sharpened tip portion 134, and a shaft portion 136 spacing apart and connecting the flattened head portion 132 and the pointed and/or sharpened tip portion 134. In some embodiments, the anchor element 130 may include an upper head portion 133 and an upper shaft portion 131 extending proximally and/or away from the flattened head portion 132 and/or the shaft portion 136, thereby spacing apart and connecting the flattened head portion 132 and the upper head portion 133. In at least some embodiments, the upper head portion 133 may have a generally flattened shape and/or may be oriented substantially parallel to the flattened head portion 132. In some embodiments, the flattened head portion 132 and/or the upper head portion 133 may extend generally perpendicular to and/or radially outward from the shaft portion 136 and/or the upper shaft portion 131.

The pointed and/or sharpened tip portion 134 may be angled and/or tapered radially inward in a distal direction and/or away from the flattened head portion 132, and may be configured to be advanced into and/or through the mitral valve leaflet tissue. The flattened head portion 132 may be configured to engage and/or rest against one side (e.g., on an atrial side, on a ventricular side) of the mitral valve leaflet tissue, for example the atrial side of the mitral valve leaflet tissue. In some embodiments, the shaft portion 136 may be configured to extend through the mitral valve leaflet tissue such that only one layer and/or a single thickness of the mitral valve leaflet tissue is disposed between the flattened head portion 132 and the pointed and/or sharpened tip portion 134. In at least some embodiments, the flattened head portion 132 may have a maximum outer extent and/or diameter greater than a maximum outer extent and/or diameter of the pointed and/or sharpened tip portion 134, wherein the maximum outer extent and/or diameter of the pointed and/or sharpened tip portion 134 may be greater than a maximum outer extent and/or diameter of the shaft portion 136. In some embodiments, a maximum outer extent and/or diameter of the upper head portion 133 may be the same as and/or less than the maximum outer extent and/or diameter of the flattened head portion 132. Other forms of fixed or expandable rivets or rivet-like fasteners, a pop rivet for example, may also be used. Some suitable but non-limiting materials for the anchor element 130, for example metallic materials, polymer materials, composite materials, etc., are described below.

Figure 4:
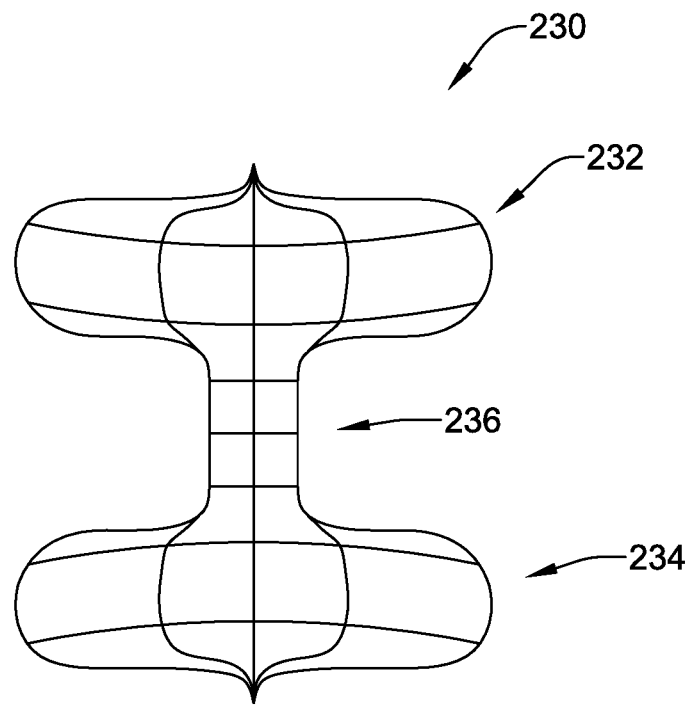
FIG. 4 illustrates an example anchor element.

FIG. 4 illustrates an alternative anchor element 230 comprising an expanding frame. In some embodiments, the expanding frame may be similar in design and/or structure to expanding frames used in stents, anchoring structures, filters, occlusive elements, etc. The anchor element 230 may be used in substantially the same manner, placement, and usage as the anchor element 130, unless explicitly noted herein. The anchor element 230 may be configured to shift between an elongated and collapsed delivery configuration (not shown), suitable for disposal in and/or delivery through the plurality of anchor lumens 120, and a radially expanded deployed configuration (e.g., FIG. 4). The anchor element 230 may include a proximal head portion 232, a distal tip portion 234, and a shaft portion 236 spacing apart and connecting the proximal head portion 232 and the distal tip portion 234. In at least some embodiments, the distal tip portion 234 may be pointed and/or sharpened to facilitate advancement through the mitral valve leaflet tissue. The proximal head portion 232 and the distal tip portion 234 may each be configured to radially expand from the elongated and collapsed delivery configuration to the radially expanded deployed configuration after being advanced out of its respective anchor lumen 120. In some embodiments, the shaft portion 236 may be configured to extend through the mitral valve leaflet tissue such that only one layer and/or a single thickness of the mitral valve leaflet tissue is disposed between the proximal head portion 232 and the distal tip portion 234. The anchor element 230 may be configured to longitudinally shorten in overall length when shifting from the elongated and collapsed delivery configuration to the radially expanded deployed configuration, thereby capturing and/or pinching the mitral valve leaflet tissue between the proximal head portion 232 and the distal tip portion 234.

In some embodiments, the proximal head portion 232 and/or the distal tip portion 234 may radially expand to generally flattened shape, similar to the flattened head portion 132 above. The proximal head portion 232 may be configured to engage and/or rest against the atrial surface of the mitral valve leaflet tissue and/or the distal tip portion 234 may be configured to engage and/or rest against a ventricular surface of the mitral valve leaflet tissue. In some embodiments, the proximal head portion 232 may expand to a maximum outer extent and/or diameter greater than a maximum outer extent and/or diameter of the distal tip portion 234, wherein the maximum outer extent and/or diameter of the distal tip portion 234 may be greater than a maximum outer extent and/or diameter of the shaft portion 236. In some embodiments, the maximum outer extent and/or diameter of the proximal head portion 232 and the maximum outer extent and/or diameter of the distal tip portion 234 may be substantially similar and/or the same. In some embodiments, the anchor element 230 may be self-expandable, mechanically-expandable, and/or combinations thereof. In some embodiments, the anchor element 230 may be formed from a shape memory material. Some suitable but non-limiting materials for the anchor element 230, for example metallic materials, polymer materials, composite materials, etc., are described below.

Figure 5:
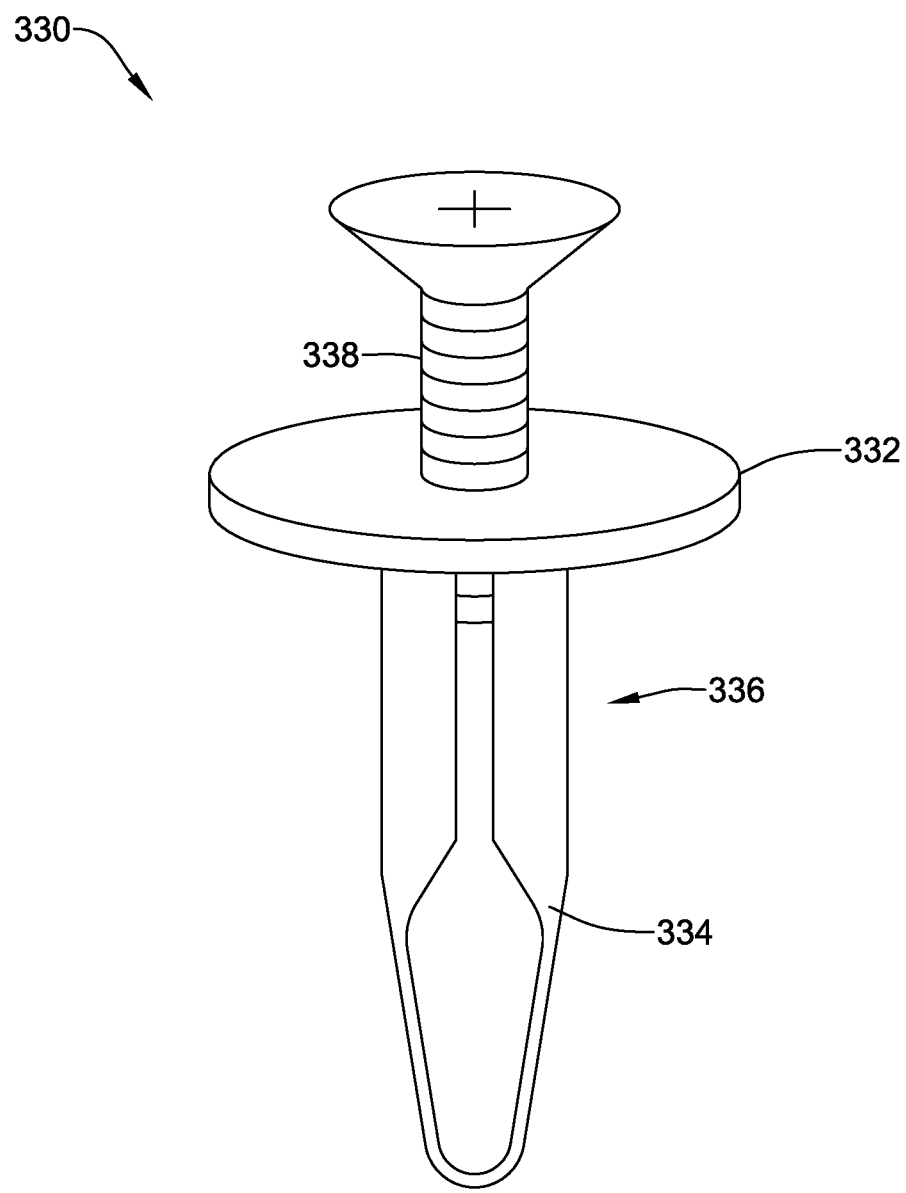
FIGS. 5-6 illustrate an example anchor element.
Figure 6:
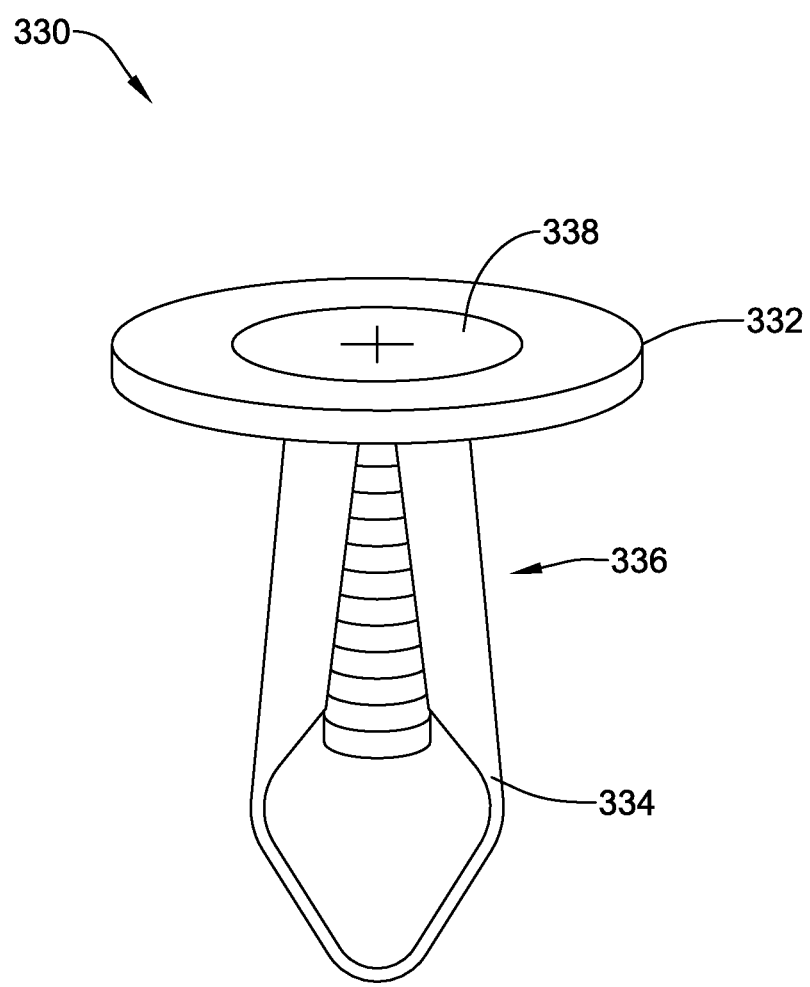

FIGS. 5 and 6 illustrate an alternative anchor element 330 comprising a screw-type fastener. The anchor element 330 may be configured to shift from a delivery configuration (e.g., FIG. 5) to a deployed configuration (e.g., FIG. 6). The anchor element 330 may include a proximal head portion 332, a distal portion 334, and a rotatable insert 338 rotatably and threadably connected to the proximal head portion 332 and/or the distal portion 334. In the delivery configuration, the distal portion 334 may include a distal taper radially inward extending from a generally uniform diameter shaft portion 336, and the rotatable insert 338 may extend through and proximally from the proximal head portion 332. Clockwise rotation of the rotatable insert 338 relative to the proximal head portion 332, the distal portion 334, and/or the shaft portion 336 of the anchor element 330, via a threaded connection for example, may advance the rotatable insert 338 distally through the proximal head portion 332 and/or into the shaft portion 336 and/or the distal portion 334. Clockwise rotation of the rotatable insert 338 relative to the proximal head portion 332, the distal portion 334, and/or the shaft portion 336 of the anchor element 330 may radially and/or laterally expand, and/or longitudinally shorten, the distal portion 334 of the anchor element 330, thereby shifting the anchor element 330 from the delivery configuration to the deployed configuration.

Counterclockwise rotation of the rotatable insert 338 relative to the proximal head portion 332, the distal portion 334, and/or the shaft portion 336 of the anchor element 330 may reverse the shift from the deployed configuration toward the delivery configuration.

The proximal head portion 332 of the anchor element 330 may be configured to engage and/or rest against one side (e.g., on an atrial side, on a ventricular side) of the mitral valve leaflet tissue. The distal portion 334 of the anchor element 330 may be angled and/or tapered radially inward in a distal direction and/or away from the proximal head portion 332, and may be configured to be advanced into and/or through the mitral valve leaflet tissue. In at least some embodiments, the distal portion 334 of the anchor element 330 may be pointed and/or sharpened to facilitate advancement through the mitral valve leaflet tissue. In some embodiments, the shaft portion 336 of the anchor element 330 may be configured to extend through the mitral valve leaflet tissue such that only one layer and/or a single thickness of the mitral valve leaflet tissue is disposed between the proximal head portion 332 and the distal portion 334 of the anchor element 330. In at least some embodiments, the proximal head portion 332 of the anchor element 330 may have a maximum outer extent and/or diameter greater than a maximum outer extent and/or diameter of the distal portion 334 of the anchor element 330, wherein the maximum outer extent and/or diameter of the distal portion 334 of the anchor element 330 in the deployed configuration may be greater than a maximum outer extent and/or diameter of the shaft portion 336 of the anchor element 330. Some suitable but non-limiting materials for the anchor element 330, for example metallic materials, polymer materials, composite materials, etc., are described below.

Figure 7:
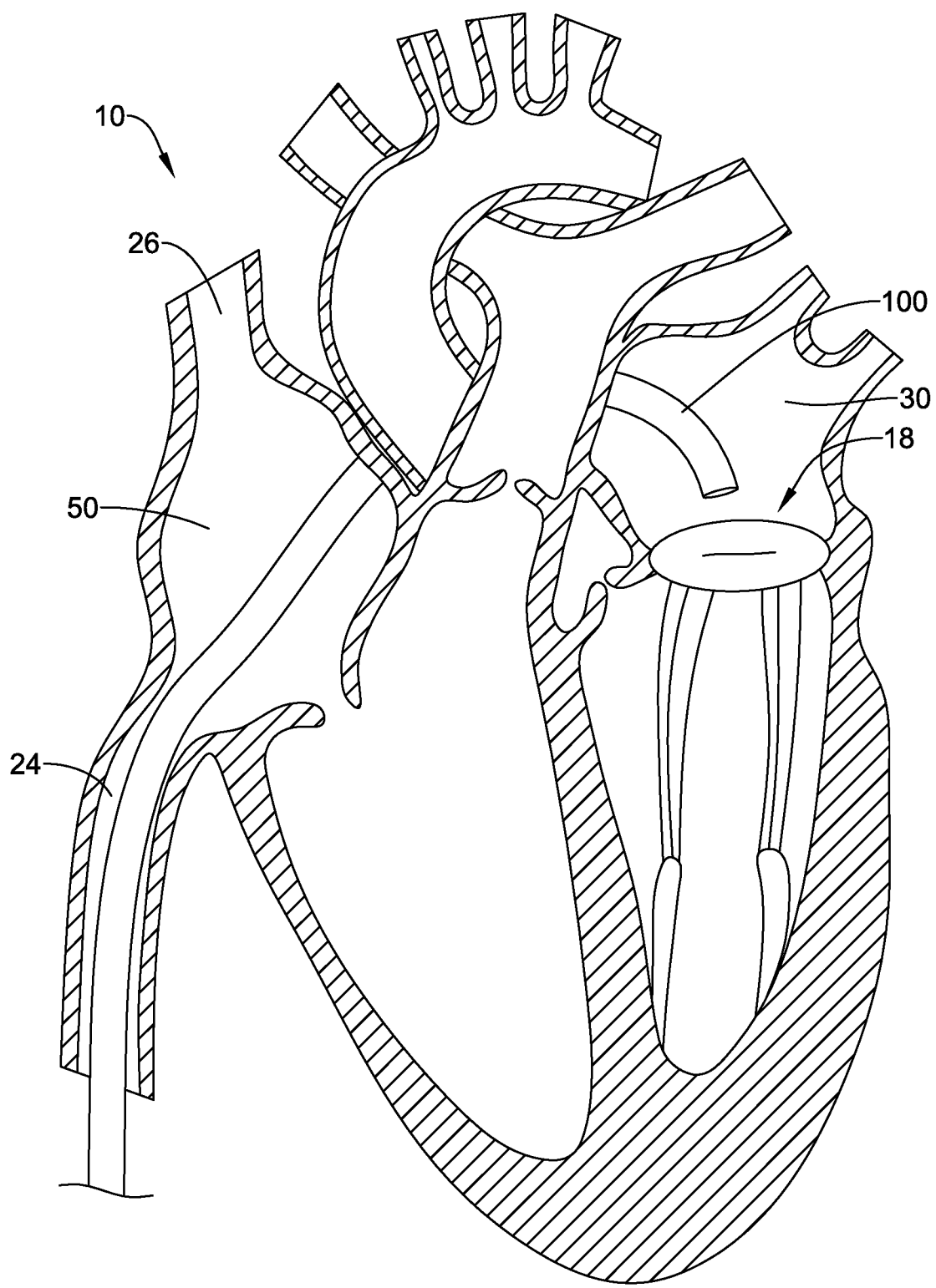
FIGS. 7-17 illustrate aspects of a method of treating mitral valve prolapse.
Figure 8:
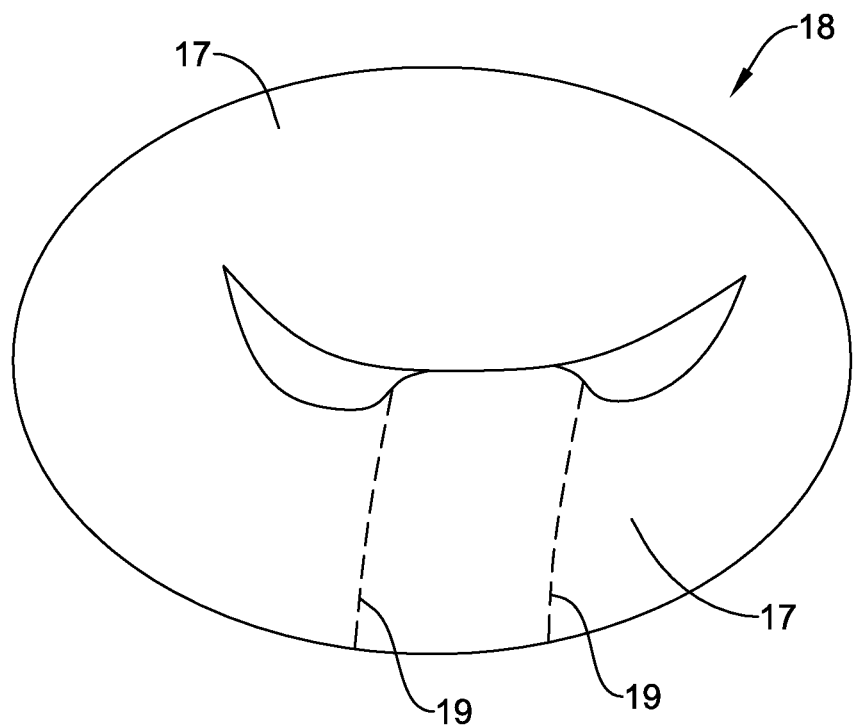

FIGS. 7-15 illustrate aspects of an example method of treating mitral valve prolapse. For example, the method may include percutaneously inserting a delivery catheter 100 through a vasculature to the left atrium 30 of the heart 10. In at least some embodiments, access to the left atrium 30 may be achieved using a transseptal approach, which may involve transiting the septum of the heart 10 between the left atrium 30 and the right atrium 50. The delivery catheter 100 may be advanced into right atrium 50 of the heart 10 through the inferior vena cava 24 or the superior vena cava 26 before transiting the septum and advancing into the left atrium 30, as shown in FIG. 7 for example. Alternative percutaneous approaches, through the aorta for example, may also be used. FIG. 8 illustrates the mitral valve 18 in a prolapsed condition, wherein a mitral valve leaflet 17 may include redundant excessive and/or prolapsed tissue in part of the mitral valve 18 that prevents proper closure and/or coaptation of the mitral valve leaflets 17. The redundant excessive and/or prolapsed tissue may be seen in FIG. 8 (and subsequent figures) between lateral boundaries 19, designated by broken lines.

Figure 9:
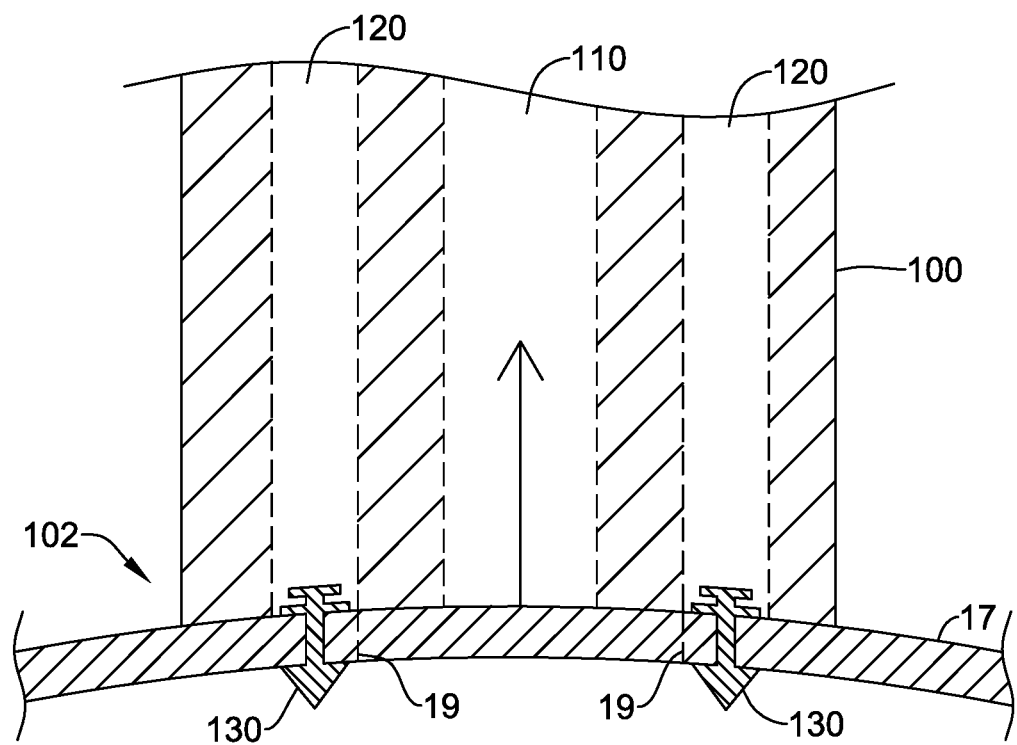
Figure 10:
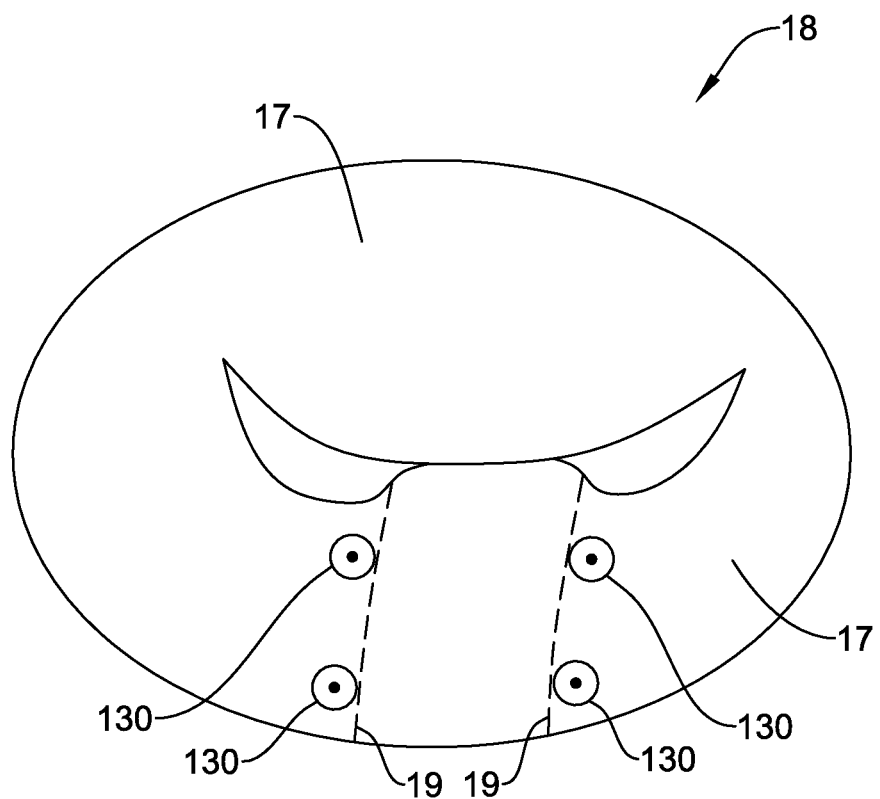

After inserting the delivery catheter 100 into the left atrium 30 of the heart 10, the method may include securing the distal end 102 of the delivery catheter 100 to the mitral valve leaflet 17 using the suction lumen 110 extending through the delivery catheter 100, as shown in FIG. 9 for example. The method may further include inserting a plurality of anchor elements 130 (e.g., 230, 330) into the mitral valve leaflet 17 from the distal end 102 of the delivery catheter 100 at spaced-apart locations, as seen in FIGS. 9 and 10. In some embodiments, the mitral valve leaflet 17 may be released from the distal end 102 of the delivery catheter 100 after inserting each anchor element 130, and the distal end 102 of the delivery catheter 100 may be re-secured to the mitral valve leaflet 17 before inserting each subsequent anchor element 130 into the mitral valve leaflet 17. The plurality of anchor elements 130 may be inserted along the lateral boundaries 19 of the prolapsed tissue of the mitral valve leaflet 17, as seen in FIG. 10, such that two of the plurality of anchor elements 130 are disposed on opposing sides of the prolapsed tissue of the mitral valve leaflet 17. In at least some embodiments, inserting the plurality of anchor elements 130 into the mitral valve leaflet 17 includes inserting each anchor element 130 through only a single layer or thickness of the mitral valve leaflet 17.

Figure 11:
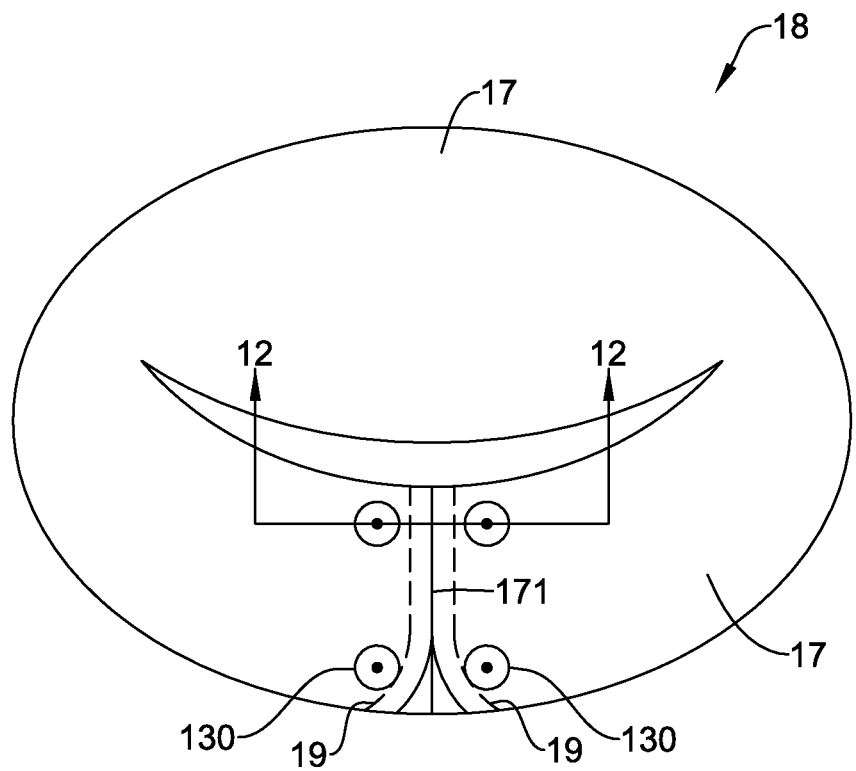
Figure 12:
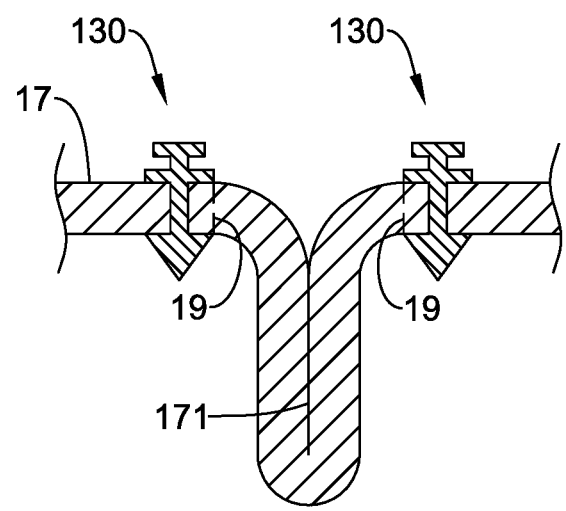

The method may include translating two of the plurality of anchor elements 130 closer together, as shown in FIG. 11, wherein translating two of the plurality of anchor elements 130 closer together further comprises forming a fold 171 in the mitral valve leaflet 17, the fold 171 being disposed between the at least two of the plurality of anchor elements 130, as seen in FIG. 12 for example, which illustrates a cross-section taken along line 12-12 in FIG. 11. In some embodiments, the fold 171 may comprise a single fold, as illustrated, or the fold 171 may comprise a plurality of folds forming an accordion-like or pleated structure. In some embodiments, the fold 171 may initiate at the lateral boundaries 19, although this is not strictly necessary. Next, the method may include securing the at least two of the plurality of anchor elements 130 together on one side (e.g., on an atrial side, on a ventricular side) of the mitral valve leaflet 17. In some embodiments, securing two of the plurality of anchor elements 130 together forms the fold 171 in the one layer of mitral valve leaflet tissue, the fold 171 being disposed between the at least two of the plurality of anchor elements 130.

Figure 13:
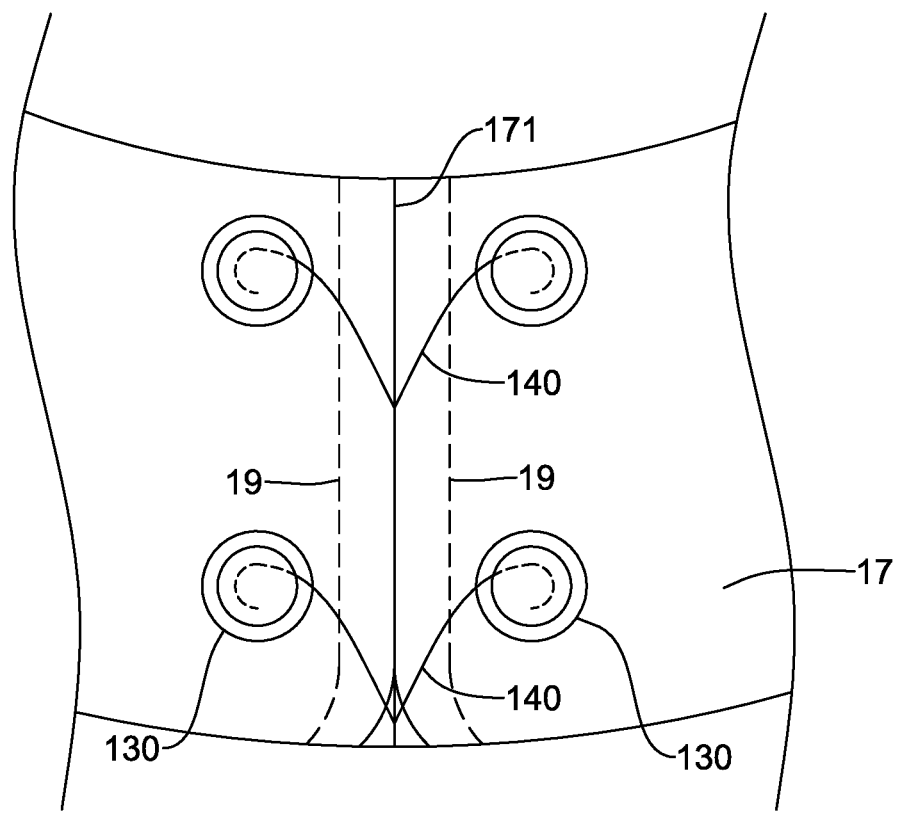
Figure 14:
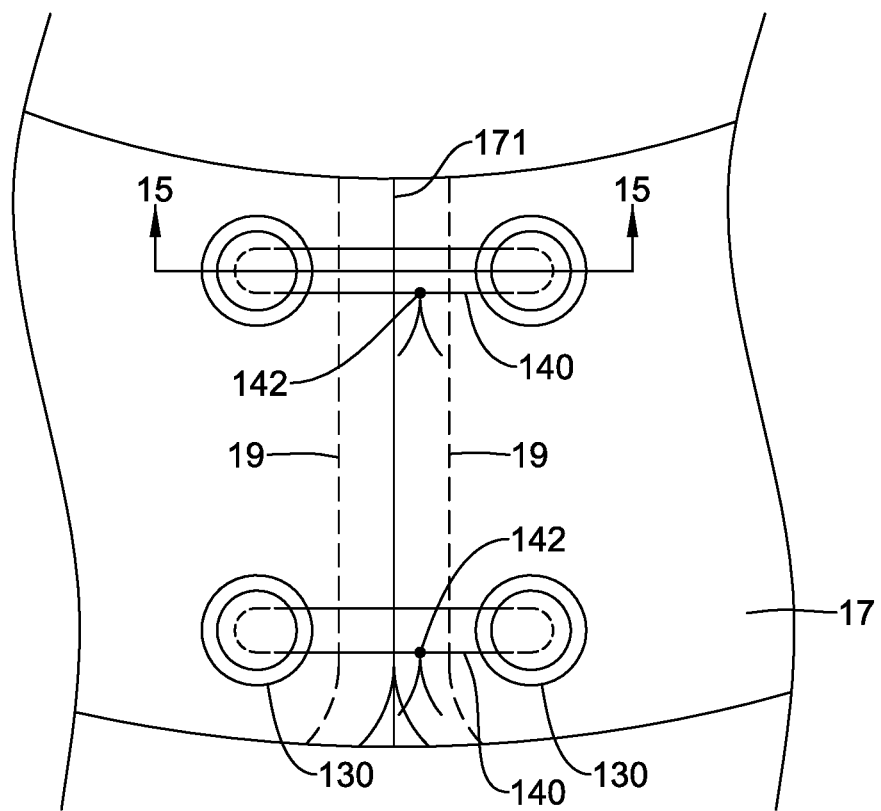
Figure 15:
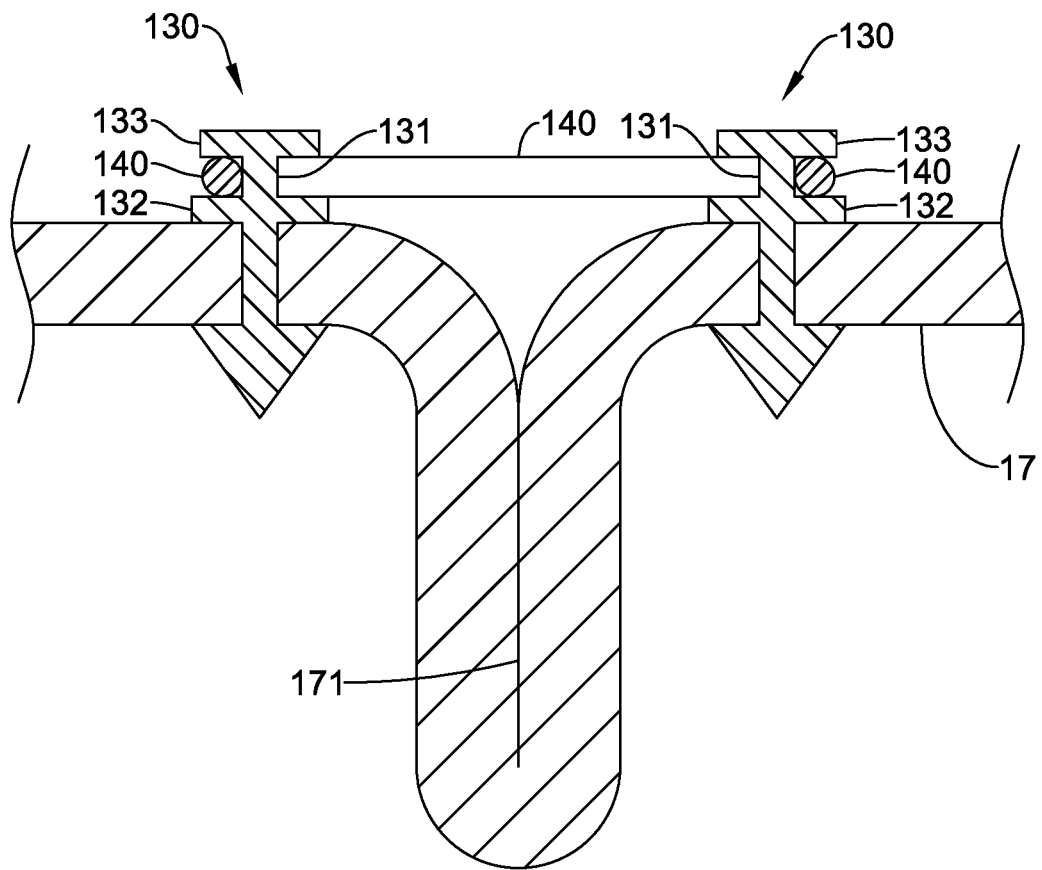

As show in FIG. 13, in some embodiments, the mitral valve leaflet repair system may include a securing element 140. In some embodiments, the securing element 140 may be delivered to the mitral valve 18 and/or the plurality of anchor elements 130 through the delivery catheter 100, the suction lumen 110, and/or one of the plurality of anchor lumens 120. Alternatively, the securing element 140 may be delivered using a separate delivery device, either alone or in conjunction with the delivery catheter 100. In some embodiments, the securing element 140 may be configured to be disposed around at least a portion of a perimeter of each of the at least two of the plurality of anchor elements 130. In some embodiments, the securing element 140 may be disposed around the upper shaft portion 131 of each anchor element 130 between the flattened head portion 132 and the upper head portion 133, as seen in FIGS. 13-15. In some embodiments, the securing element 140 may be configured to translate each pair of the at least two of the plurality of anchor elements 130 closer together. In at least some embodiments, the securing element 140 may comprise a shape memory material. In some embodiments, the securing element 140 may comprise a suture, a wire, and/or a filament. In some embodiments, the securing element 140 may form a closed loop around the at least two of the plurality of anchor elements 130 (e.g., FIG. 14). In some embodiments, the securing element 140 may comprise a magnetic attraction between each of the at least two of the plurality of anchor elements 130. For example, each anchor element 130 may include and/or be formed from a magnetic material, may include a magnetic element disposed within the anchor element 130 (e.g., within the flattened head portion 132, within the pointed and/or sharpened tip portion 134, and/or within the shaft portion 136, etc.). Some suitable but non-limiting materials for the securing element 140, for example metallic materials, polymer materials, composite materials, etc., are described below.

In some embodiments, the at least two of the plurality of anchor elements 130 may be secured together on only one side of the mitral valve leaflet 17 (e.g., the atrial side, the ventricular side, etc.) and/or the mitral valve leaflet tissue. In some embodiments, the at least two of the plurality of anchor elements 130 may be secured together on both sides (e.g., the atrial side and the ventricular side) of the mitral valve leaflet 17 and/or the mitral valve leaflet tissue. In some embodiments, the at least two of the plurality of anchor elements 130 may be secured together on only one side of the mitral valve leaflet 17 without the securing element 140 passing through the mitral valve leaflet 17 and/or the mitral valve leaflet tissue. In some embodiments, the at least two of the plurality of anchor elements 130 may be secured together on both sides of the mitral valve leaflet 17 without the securing element 140 passing through the mitral valve leaflet 17 and/or the mitral valve leaflet tissue. In some embodiments, the mitral valve leaflet repair system may include at least two securing elements 140, wherein a first securing element 140 is disposed on the atrial side of the mitral valve leaflet 17 and/or the mitral valve leaflet tissue, and a second securing element 140 is disposed on the ventricular side of the mitral valve leaflet 17 and/or the mitral valve leaflet tissue. Various combinations of the securing element 140 described herein may be used in embodiments having more than one securing element 140.

In an alternative embodiment, the method may include inserting two or more pairs of anchor elements 130 into the mitral valve leaflet 17 from the distal end 102 of the delivery catheter 100 at a first relative location (seen in FIG. 10 for example), wherein the anchor elements 130 of each pair of anchor elements 130 are spaced apart from each other at the first relative location. The two or more pairs of anchor elements 130 may be disposed within lumens of the delivery catheter 100 other than the suction lumen 110 (for example, at least one of the plurality of anchor lumens 120, etc.) prior to insertion into the mitral valve leaflet 17. In some embodiments, each pair of anchor elements 130 may be disposed within a corresponding pair of anchor lumens 120 disposed opposite each other relative to the suction lumen 110, and/or on opposing sides of the suction lumen 110.

The mitral valve leaflet 17 may be released from the distal end 102 of the delivery catheter 100 after inserting each pair of anchor elements 130, and the distal end 102 of the delivery catheter 100 may be re-secured to the mitral valve leaflet 17 before inserting each subsequent pair of anchor elements 130 into the mitral valve leaflet 17. Each pair of anchor elements 130 may be inserted along the lateral boundaries 19 of the prolapsed tissue of the mitral valve leaflet 17, such that each anchor element of each pair of anchor elements 130 is disposed on opposing sides of the prolapsed tissue of the mitral valve leaflet 17. In at least some embodiments, inserting two of more pairs of anchor elements 130 into the mitral valve leaflet 17 includes inserting each pair of anchor elements 130 through only a single layer or thickness of the mitral valve leaflet 17.

An alternative method may include translating each pair of anchor elements 130 to a second relative location, as seen in FIG. 11 for example, wherein the anchor elements 130 of each pair of anchor elements 130 are closer together than at the first relative location. In some embodiments, the securing element 140 may be configured to translate each pair of anchor elements 130 to the second relative location. Translating each pair of anchor elements 130 to the second relative location may further comprise forming a fold 171 in the mitral valve leaflet 17, the fold 171 being disposed between each pair of anchor elements 130, as seen in FIG. 12. In some embodiments, the method may include securing each pair of anchor elements 130 together at the second relative location on one side of the mitral valve leaflet 17, as seen in FIGS. 13-15, with the fold 171 being disposed between each pair of anchor elements 130.

In some embodiments, the securing element 140 may be configured to be disposed around at least a portion of a perimeter of each pair of anchor elements 130. In some embodiments, the securing element 140 may be disposed around the upper shaft portion 131 of each anchor element 130 between the flattened head portion 132 and the upper head portion 133, as seen in FIGS. 13-15. In at least some embodiments, the securing element 140 may comprise a shape memory material. In some embodiments, the securing element 140 may comprise a suture, a wire, and/or a filament. As shown in FIG. 14, the securing element 140 may form a closed loop around each pair of anchor elements 130, the closed loop being held closed and/or secured by a securement member 142. The securement member 142 may comprise a knot, a cinch, a crimp, or other suitable means of securing the securing element 140 to itself, where necessary. In some embodiments, the securing element 140 may comprise a magnetic attraction between each pair of anchor elements 130. For example, each anchor element 130 may include and/or be formed from a magnetic material, may include a magnetic element disposed within the anchor element 130 (e.g., within the flattened head portion 132, within the pointed and/or sharpened tip portion 134, and/or within the shaft portion 136, etc.).

Some additional details are illustrated in FIG. 15, which is cross-section taken along line 15-15 of FIG. 14. The configuration(s) and/or general arrangement(s) shown in FIG. 15 may also apply to the embodiment(s) shown in FIG. 13. In some embodiments, each pair of anchor elements 130 may be secured together on only one side of the mitral valve leaflet 17 (e.g., the atrial side, the ventricular side, etc.) and/or the mitral valve leaflet tissue. In some embodiments, each pair of anchor elements 130 may be secured together on both sides (e.g., the atrial side and the ventricular side) of the mitral valve leaflet 17 and/or the mitral valve leaflet tissue. In some embodiments, each pair of anchor elements 130 may be secured together on only one side of the mitral valve leaflet 17 without the securing element 140 passing through the mitral valve leaflet 17 and/or the mitral valve leaflet tissue. In some embodiments, each pair of anchor elements 130 may be secured together on both sides of the mitral valve leaflet 17 without the securing element 140 passing through the mitral valve leaflet 17 and/or the mitral valve leaflet tissue. In some embodiments, the mitral valve leaflet repair system may include at least two securing elements 140, wherein a first securing element 140 is disposed on the atrial side of the mitral valve leaflet 17 and/or the mitral valve leaflet tissue, and a second securing element 140 is disposed on the ventricular side of the mitral valve leaflet 17 and/or the mitral valve leaflet tissue. Various combinations of the securing element 140 described herein may be used in embodiments having more than one securing element 140.

Figure 16:
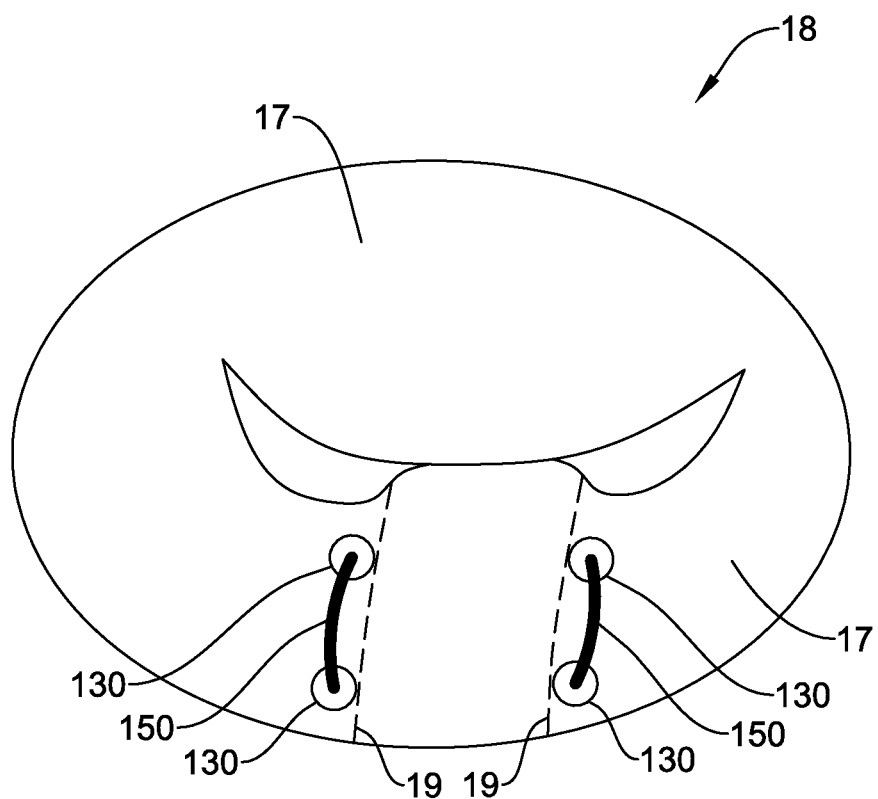

In another alternative embodiment, the method may include inserting two or more pairs of anchor elements 130 into the mitral valve leaflet 17 from the distal end 102 of the delivery catheter 100 at a first relative location, as seen in FIG. 16, wherein the anchor elements 130 of each pair of anchor elements 130 are spaced apart from each other at the first relative location. The two or more pairs of anchor elements 130 may be disposed within lumens of the delivery catheter 100 other than the suction lumen 110 (for example, at least one of the plurality of anchor lumens 120, etc.) prior to insertion into the mitral valve leaflet 17. In some embodiments, each pair of anchor elements 130 may be disposed within a corresponding pair of anchor lumens 120 disposed opposite each other relative to the suction lumen 110, and/or on opposing sides of the suction lumen 110.

The mitral valve leaflet 17 may be released from the distal end 102 of the delivery catheter 100 after inserting each pair of anchor elements 130, and the distal end 102 of the delivery catheter 100 may be re-secured to the mitral valve leaflet 17 before inserting each subsequent pair of anchor elements 130 into the mitral valve leaflet 17. Each anchor element of each pair of anchor elements 130 may be inserted and/or positioned along the lateral boundaries 19 of the prolapsed tissue of the mitral valve leaflet 17. In some embodiments, a linking element 150 may extend between adjacent anchor elements 130 along each of the lateral boundaries 19. As such, there may be at least one linking element 150 positioned along and/or generally parallel to each of the lateral boundaries 19. In at least some embodiments, inserting two of more pairs of anchor elements 130 into the mitral valve leaflet 17 includes inserting each pair of anchor elements 130 through only a single layer or thickness of the mitral valve leaflet 17. In some embodiments, there may be a linking element 150 disposed on each side (e.g., the atrial side and the ventricular side) of the mitral valve leaflet 17.

Figure 17:
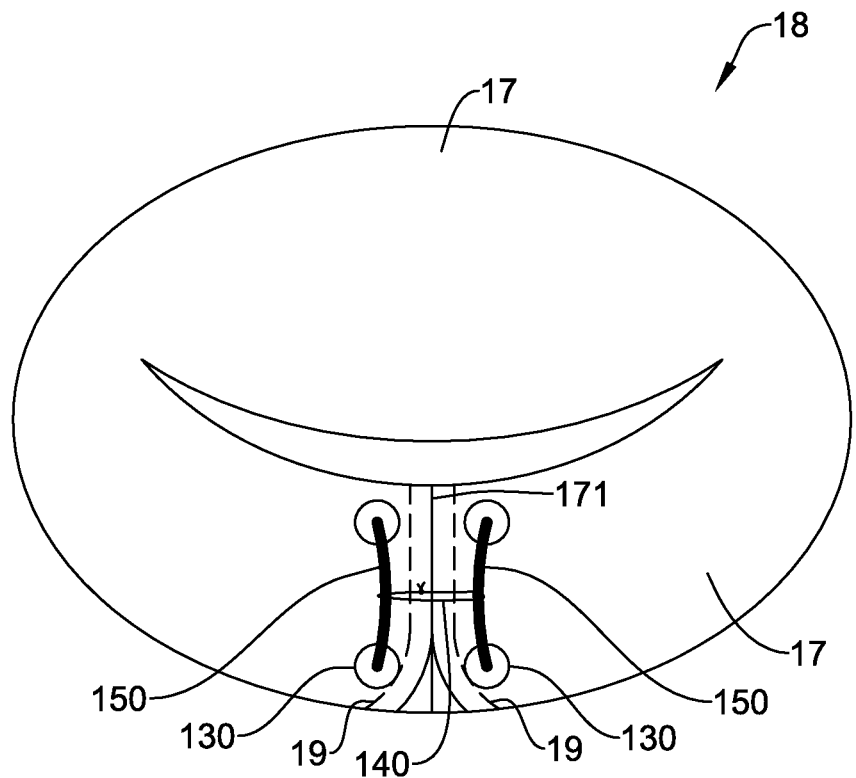

An alternative method may include translating each pair of anchor elements 130 to a second relative location, as seen in FIG. 17 for example, wherein the anchor elements 130 of each pair of anchor elements 130 are closer together than at the first relative location. Translating each pair of anchor elements 130 to the second relative location may further comprise forming a fold 171 in the mitral valve leaflet 17. In some embodiments, the method may include securing the linking element(s) 150 between adjacent anchor elements 130 along each of the lateral boundaries 19 together to bring each pair of anchor elements 130 together at the second relative location on one side of the mitral valve leaflet 17 with the securing element 140, as seen in FIG. 17.

In some embodiments, the securing element 140 may be configured to be disposed around at least a portion of a perimeter of each pair of anchor elements 130, in the manner described above. For example, in some embodiments, the securing element 140 may be disposed around the upper shaft portion 131 of each anchor element 130 between the flattened head portion 132 and the upper head portion 133 (e.g., FIGS. 13-15). In some embodiments, the securing element 140 may comprise a shape memory material. In some embodiments, the securing element 140 may comprise a suture, a wire, and/or a filament. In some embodiments, the securing element 140 may form a closed loop around each of the linking elements 150 (e.g., FIG. 17).

In some embodiments, each pair of anchor elements 130 and/or the linking elements 150 may be secured together on only one side of the mitral valve leaflet 17 (e.g., the atrial side, the ventricular side, etc.) and/or the mitral valve leaflet tissue. In some embodiments, each pair of anchor elements 130 and/or the linking elements 150 may be secured together on both sides (e.g., the atrial side and the ventricular side) of the mitral valve leaflet 17 and/or the mitral valve leaflet tissue. In some embodiments, each pair of anchor elements 130 and/or the linking elements 150 may be secured together on only one side of the mitral valve leaflet 17 without the securing element 140 passing through the mitral valve leaflet 17 and/or the mitral valve leaflet tissue. In some embodiments, each pair of anchor elements 130 and/or the linking elements 150 may be secured together on both sides of the mitral valve leaflet 17 without the securing element 140 passing through the mitral valve leaflet 17 and/or the mitral valve leaflet tissue. In some embodiments, the mitral valve leaflet repair system may include at least two securing elements 140, wherein a first securing element 140 is disposed on the atrial side of the mitral valve leaflet 17 and/or the mitral valve leaflet tissue, and a second securing element 140 is disposed on the ventricular side of the mitral valve leaflet 17 and/or the mitral valve leaflet tissue. Various combinations of the securing element 140 described herein may be used in embodiments having more than one securing element 140.

The materials that can be used for the various components of the mitral valve leaflet repair system, the delivery catheter 100, the anchor elements 130/230/330, the securing elements 140, the linking elements 150, etc. (and/or other systems or components disclosed herein) and the various elements thereof disclosed herein may include those commonly associated with medical devices. For simplicity purposes, the following discussion makes reference to the mitral valve leaflet repair system, the delivery catheter 100, the anchor elements 130/230/330, the securing elements 140, the linking elements 150, etc. However, this is not intended to limit the devices and methods described herein, as the discussion may be applied to other elements, members, components, or devices disclosed herein, such as, but not limited to, the upper shaft portion 131, the head portion 132/232/332, the upper head portion 133, the distal portion 134/234/334, the shaft portion 136/236/336, the rotatable insert 338, etc. and/or elements or components thereof.

In some embodiments, the mitral valve leaflet repair system, the delivery catheter 100, the anchor elements 130/230/330, the securing elements 140, the linking elements 150, etc., and/or components thereof may be made from a metal, metal alloy, polymer (some examples of which are disclosed below), a metal-polymer composite, ceramics, combinations thereof, and the like, or other suitable material. Some examples of suitable metals and metal alloys include stainless steel, such as 444V, 444L, and 314LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R44035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R44003 such as ELGILOY®, PHYNOX®, and the like); platinum enriched stainless steel; titanium; platinum, platinum-iridium, other platinum alloys; palladium; gold; combinations thereof;

and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear than the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the mitral valve leaflet repair system, the delivery catheter 100, the anchor elements 130/230/330, the securing elements 140, the linking elements 150, etc., and/or components thereof, may also be doped with, made of, or otherwise include a radiopaque material. Radiopaque materials are understood to be materials capable of producing a relatively bright image on a fluoroscopy screen or another imaging technique during a medical procedure. This relatively bright image aids a user in determining the location of the mitral valve leaflet repair system, the delivery catheter 100, the anchor elements 130/230/330, the securing elements 140, the linking elements 150, etc. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the mitral valve leaflet repair system, the delivery catheter 100, the anchor elements 130/230/330, the securing elements 140, the linking elements 150, etc. to achieve the same result.

In some embodiments, a degree of Magnetic Resonance Imaging (MRI) compatibility is imparted into the mitral valve leaflet repair system, the delivery catheter 100, the anchor elements 130/230/330, the securing elements 140, the linking elements 150, etc. For example, the mitral valve leaflet repair system, the delivery catheter 100, the anchor elements 130/230/330, the securing elements 140, the linking elements 150, etc., and/or components or portions thereof, may be made of a material that does not substantially distort the image and create substantial artifacts (e.g., gaps in the image). Certain ferromagnetic materials, for example, may not be suitable because they may create artifacts in an MRI image. The mitral valve leaflet repair system, the delivery catheter 100, the anchor elements 130/230/330, the securing elements 140, the linking elements 150, etc., or portions thereof, may also be made from a material that the MRI machine can image. Some materials that exhibit these characteristics include, for example, tungsten, cobalt-chromium-molybdenum alloys (e.g., UNS: R44003 such as ELGILOY®, PHYNOX®, and the like), nickel-cobalt-chromium-molybdenum alloys (e.g., UNS: R44035 such as MP35-N® and the like), nitinol, and the like, and others.

In some embodiments, the mitral valve leaflet repair system, the delivery catheter 100, the anchor elements 130/230/330, the securing elements 140, the linking elements 150, etc., and/or portions thereof, may be made from or include a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, polyurethane silicone copolymers (for example, ElastEon® from Aortech Biomaterials or ChronoSil® from AdvanSource Biomaterials), biocompatible polymers, other suitable materials, or mixtures, combinations, copolymers thereof, polymer/metal composites, and the like. In some embodiments, the sheath can be blended with a liquid crystal polymer (LCP). For example, the mixture can contain up to about 6 percent LCP.

In some embodiments, the mitral valve leaflet repair system, the delivery catheter 100, the anchor elements 130/230/330, the securing elements 140, the linking elements 150, etc. may include and/or be formed from a textile material. Some examples of suitable textile materials may include synthetic yarns that may be flat, shaped, twisted, textured, pre-shrunk or un-shrunk. Synthetic biocompatible yarns suitable for use in the present invention include, but are not limited to, polyesters, including polyethylene terephthalate (PET) polyesters, polypropylenes, polyethylenes, polyurethanes, polyolefins, polyvinyls, polymethylacetates, polyamides, naphthalene dicarboxylene derivatives, natural silk, and polytetrafluoroethylenes. Moreover, at least one of the synthetic yarns may be a metallic yarn or a glass or ceramic yarn or fiber. Useful metallic yarns include those yarns made from or containing stainless steel, platinum, gold, titanium, tantalum or a Ni—Co—Cr-based alloy. The yarns may further include carbon, glass or ceramic fibers. Desirably, the yarns are made from thermoplastic materials including, but not limited to, polyesters, polypropylenes, polyethylenes, polyurethanes, polynaphthalenes, polytetrafluoroethylenes, and the like. The yarns may be of the multifilament, monofilament, or spun-types. The type and denier of the yarn chosen may be selected in a manner which forms a biocompatible and implantable prosthesis and, more particularly, a vascular structure having desirable properties.

In some embodiments, the mitral valve leaflet repair system, the delivery catheter 100, the anchor elements 130/230/330, the securing elements 140, the linking elements 150, etc. may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethylketone)); anti-proliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vasoactive mechanisms.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. A mitral valve leaflet repair system, comprising:
a delivery catheter having at least four lumens extending proximally from a distal end of the delivery catheter;
two or more pairs of anchor elements disposed within the at least four lumens, each of the two or more pairs of anchor elements being configured to extend through one layer of a mitral valve leaflet tissue; and
a securing element configured to secure at least two anchor elements of the two or more pairs of anchor elements together on one side of the mitral valve leaflet tissue;
wherein at least one lumen of the at least four lumens comprises a suction lumen configured to grasp a mitral valve leaflet prior to extending the two or more pairs of anchor elements through one layer of mitral valve leaflet tissue;
wherein the securing element is configured to be disposed around at least a portion of a perimeter of each of two anchor elements of the two or more pairs of anchor elements.

2. The mitral valve leaflet repair system of claim 1, wherein at least one anchor element of the two or more pairs of anchor elements is disposed within each of two or more of the at least four lumens.

3. The mitral valve leaflet repair system of claim 1, wherein at least one anchor element of the two or more pairs of anchor elements is disposed within the suction lumen.

4. The mitral valve leaflet repair system of claim 1, wherein at least one anchor element of the two or more pairs of anchor elements comprises a rivet.

5. The mitral valve leaflet repair system of claim 1, wherein at least one anchor element of the two or more pairs of anchor elements comprises a self-expanding frame.

6. The mitral valve leaflet repair system of claim 1, wherein at least one anchor element of the two or more pairs of anchor elements comprises a screw-type fastener, wherein rotation of a rotatable insert expands a distal portion of its respective anchor element.

7. The mitral valve leaflet repair system of claim 1, wherein securing two anchor element of the two or more pairs of anchor elements together forms a fold in the one layer of mitral valve leaflet tissue, the fold being disposed between the at least two of the two or more pairs of anchor elements.

8. The mitral valve leaflet repair system of claim 1, wherein the securing element comprises a shape memory material.

9. The mitral valve leaflet repair system of claim 1, wherein the securing element forms a closed loop around the at least two anchor elements of the two or more pairs of anchor elements.

10. A mitral valve leaflet repair system, comprising:
a delivery catheter having at least one lumen extending proximally from a distal end of the delivery catheter;
a plurality of anchor elements disposed within the at least one lumen, each of the plurality of anchor elements being configured to extend through one layer of mitral valve leaflet tissue; and
a securing element configured to secure at least two of the plurality of anchor elements together on one side of the mitral valve leaflet tissue;
wherein the at least one lumen comprises a suction lumen configured to grasp a mitral valve leaflet prior to extending the plurality of anchor elements through one layer of mitral valve leaflet tissue;
wherein the securing element comprises a magnetic attraction between each of the at least two of the plurality of anchor elements.

11. The mitral valve leaflet repair system of claim 10, wherein the at least one lumen further comprises a plurality of anchor lumens, wherein at least one of the plurality of anchor elements is disposed within each of two or more of the plurality of anchor lumens.

12. The mitral valve leaflet repair system of claim 10, wherein at least one of the plurality of anchor elements is disposed within the suction lumen.

13. The mitral valve leaflet repair system of claim 10, wherein at least one of the plurality of anchor elements comprises a rivet.

14. The mitral valve leaflet repair system of claim 10, wherein at least one of the plurality of anchor elements comprises a self-expanding frame.

15. The mitral valve leaflet repair system of claim 10, wherein at least one of the plurality of anchor elements comprises a screw-type fastener, wherein rotation of a rotatable insert expands a distal portion of its respective anchor element.

16. The mitral valve leaflet repair system of claim 10, wherein securing two of the plurality of anchor elements together forms a fold in the one layer of mitral valve leaflet tissue, the fold being disposed between the at least two of the plurality of anchor elements.

17. A method of treating mitral valve prolapse, comprising:
percutaneously inserting a delivery catheter to a left atrium of a heart;
securing a distal end of the delivery catheter to a mitral valve leaflet using a suction lumen extending through the delivery catheter;
inserting two or more pairs of anchor elements into the mitral valve leaflet from the distal end of the delivery catheter at a first relative location, wherein the anchor elements of each pair of anchor elements are spaced apart from each other at the first relative location;
translating each pair of anchor elements to a second relative location, wherein the anchor elements of each pair of anchor elements are closer together than at the first relative location; and
securing each pair of anchor elements together at the second relative location on one side of the mitral valve leaflet;
wherein translating each pair of anchor elements to the second relative location further comprises forming a fold in the mitral valve leaflet, the fold being disposed between each pair of anchor elements.

18. The method of claim 17, wherein inserting two or more pairs of anchor elements into the mitral valve leaflet includes inserting each anchor element through only a single thickness of the mitral valve leaflet.

19. The method of claim 17, wherein the mitral valve leaflet is released from the distal end of the delivery catheter after inserting each pair of anchor elements, and the distal end of the delivery catheter is re-secured to the mitral valve leaflet before inserting each subsequent pair of anchor elements into the mitral valve leaflet.

20. The method of claim 17, wherein the two or more pairs of anchor elements are disposed within lumens of the delivery catheter other than the suction lumen prior to insertion into the mitral valve leaflet.

* * * * *